United States Patent [19]

Del Medico

[11] Patent Number: 4,913,144
[45] Date of Patent: Apr. 3, 1990

[54] ADJUSTABLE STAPLE

[75] Inventor: Nilli Del Medico, Orbassano, Italy

[73] Assignee: D.A.O. s.r.l., Turin, Italy

[21] Appl. No.: 309,324

[22] Filed: Feb. 9, 1989

[30] Foreign Application Priority Data

Aug. 3, 1988 [IT] Italy ............................ 53347/88[U]

[51] Int. Cl.⁴ ...................... A61B 17/04; A61F 5/04; F16B 15/00
[52] U.S. Cl. .................................... 606/75; 411/470; 411/450; 411/457
[58] Field of Search ................ 128/335, 334 C, 92 Y, 128/92 YC, 92 YE, 92 YF, 92 VY, 91 ZK, 92 ZY, 92 R; 411/469, 450, 457

[56] References Cited

U.S. PATENT DOCUMENTS 3,807,394 4/1974 Attenborough ............. 128/92 YC

FOREIGN PATENT DOCUMENTS 1114407 9/1984 U.S.S.R. ...................... 128/92 YC

Primary Examiner—Edward M. Coven
Assistant Examiner—Gary Jackson
Attorney, Agent, or Firm—Paul & Paul

[57] ABSTRACT

An adjustable staple to be used in bone surgery, comprising a horizontally laying U-shaped member having upper and lower arms wherein the lower arm is movable parallel to itself, and relative to the upper arm, and with the upper arm being fixed, a connecting segment between the arms, including means facilitating relative movement between the arms and means facilitating fastening of the lower arm in any selected position along said movement, said means facilitating movement including a dovetail joint between a first portion of the connecting segment orthogonal to the upper arm and a second portion of the connecting segment orthogonal to the lower arm.

3 Claims, 1 Drawing Sheet

ADJUSTABLE STAPLE

BACKGROUND OF THE INVENTION

The present invention relates to an adjustable span staple, particularly useful in the technique of bone surgery.

It is known that until presently, for example in order to straighten a bone, the usual practice is to carry out an osteotomy of such bone, consisting of a more or less deep transverse wedge cut of the concerned bone, a correct positioning of the concerned portion of such bone by drawing together the two faces of the cut until they match, then fixing the two portions, above and below the osteotomy, by means of a staple, and finally plastering the limb until the bone structure has knitted.

A typical situation is a crooked leg, that is where the shinbone has to be straightened out by aligning it with the thighbone; in such a case the osteotomy is carried out on the shinbone, the lower portion of the shinbone, below the cut, is straightened out and correctly positioned, and then fastened in such position through a staple which is driven into the shinbone above and below the osteotomy, thus maintaining the two bone portions in proper relationship. Thereafter, as stated above, a plaster also covering the thighbone is applied to the limb until the bone recovers.

It is clear that in such a situation the limb, a leg in the present case, is to be immobilized for at least forty days and the knee joint cannot be used, neither can the patient rest on the foot.

In the known art, such as the above mentioned case of a shinbone operation, the employed staples have fixed spans, i.e. the distance between the upper arm and the lower arm is fixed and predetermined for each type of staple, so that a large number of these staples are required in a hospital since the cuts are different each time as for what concerns the extension, the depth and so on.

SUMMARY OF THE INVENTION

The object of the present invention is to overcome the above shortcomings by providing an adjustably spanning staple which besides the consistent advantage of drastically reducing the number of staples required in a hospital or orthopedic clinic, provides for the outstanding advantage of avoiding the plastering after the surgical operation, a post-operative bandaging being enough, so that the patient can immediately move the limb joint, e.g. the knee joint, and as a matter of fact is able to rest on the leg one or two days after the operation.

Thus the surgeon's task is greately helped and the surgical operation is rendered quicker and more practical, as well as less annoying for the patient no longer forced to immobility.

The present adjustable staple comprises a horizontally laying U-shaped member having upper and lower tabs wherein the upper tab of the U dash-shaped member forms an upper arm of the staple, the lower tab forming a lower arm of the staple, and a connecting segment of the tabs oriented substantially orthogonally to the two arms, including means facilitating movement of the lower arm of the staple parallel to and relative to the upper fixed arm, and means facilitating fastening in any selected position along said movement; said means facilitating movement including a dovetail joint between a first portion of the connecting segment orthogonal to the upper arm and a second portion of the connecting segment orthogonal to the lower arm; said movement of the portions being capable of being manually carried out.

The means facilitates fastening of the present invention comprises socket head screws for fastening the movable arm with respect to the fixed arm. For example, a polygonal socket may be utilized so as to be easily driven by a control rod having the cross section.

A further characteristic of the present invention resides in that the staple movable arm can be fitted on the first portion of the connecting segment pertaining to the fixed arm in a reversed position, that is, in such a way as to present the movable arm in a decidedly nearer position to the parallel fixed arm, to allow contact between the two arms of the staple.

The invention will now be disclosed with particular reference to the attached drawings, illustrating a non limiting embodiment.

DESCRIPTION OF PREFERRED EMBODIMENT

Figure 1:
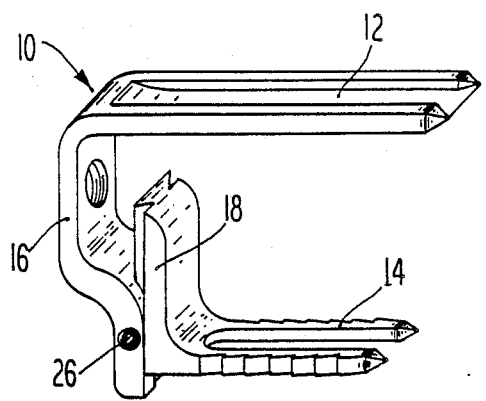
FIG. 1 is a perspective view of the staple of the invention with the movable arm slightly raised.
Figure 2:
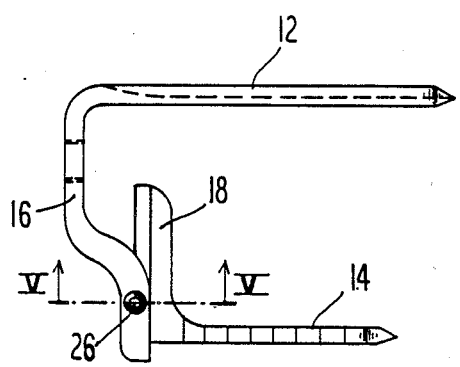
FIG. 2 is an elevation side view of the staple of FIG. 1.
Figure 3:
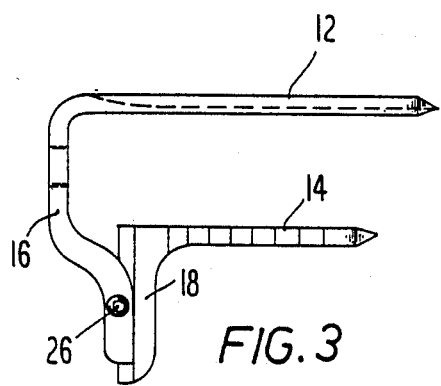
FIG. 3 is an elevation side view of the staple of FIG. 1 with the movable arm overturned.
Figure 4:
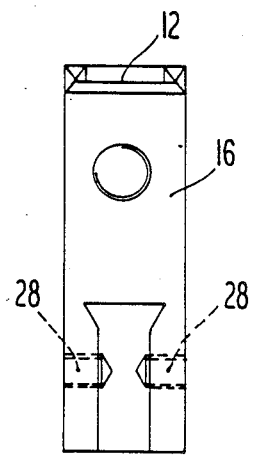
FIG. 4 is a front view of the upper (fixed) arm of the staple.
Figure 5:
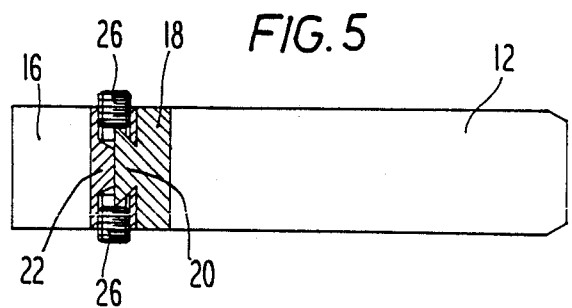
FIG. 5 is a cross section along line V—V of FIG. 2.

As clearly illustrated in the Figures, the staple of the invention is substantially similar to the conventional staples with a fixed distance between the arms, of the type usually employed in bone surgery.

The staple is substantially formed as a horizontally laying U-shaped member having upper and lower tabs, 12 and 14 respectively, the upper tab 12 of the U-shaped member forming an upper fixed arm, the lower tab 14 forming a moveable arm, and a connecting segment 16 between tabs 12 and 14 oriented substantially orthogonally the tabs 12 and 14. The staple further comprises means facilitating movement wherein the lower tab 14 is moveable in respect of the upper fixed tab 12, the relative displacement between the moveable tab 14 and the fixed tab 12 taking place along a direction which is parallel to the connecting segment 16 between the two tabs 12 and 14. In the present embodiment, said means facilitating movement comprises a dovetail joint 18 between a first portion 20 of the connecting segment 16 pertaining to the fixed tab 12, and a second portion 22 of the connecting segment 16 pertaining to the moveable tab 14. Said two portions 20 and 22 can therefore slide in respect of each other, shifting the moveable tab 14 in a direction towards the fixed tab 12, thereby achieving any desired degree of displacement between the tabs 12 and 14. Said shifting is accomplished by an operator.

Once the desired displacement has been reached, the fastening of the moveable tab 14 with respect to the fixed tab 12 is obtained by means facilitating fastening. In the preferred embodiment socket head screw means 26 engage opposing threaded seats 28 located in the first portion 20 of the connecting segment 16 pertaining to the fixed tab 12, which when tightened exert a pressure against the dovetail joint 18 of the second portion 22 of the connecting segment 16 pertaining to the moveable tab 14. The tightening of the screw means 26 and the consequent pressure over the second portion 22 fix the relative displacement of the two tabs 12 and 14.

It is to be noted that the moveable tab 14 of the staple can be mounted on the first portion 20 of the connecting segment 16 pertaining to the fixed tab 12 in a reversed position such as to position the moveable tab 14 decidedly nearer to the fixed tab 12, to allow for, as a limit, contact between the two tabs 12 and 14 of the staple.

I claim:

1. An adjustable staple to be used in bone surgery, comprising a horizontally laying U-shaped member having upper and lower tabs wherein the upper tab of the U-shaped member forms an upper arm of the staple, the lower tab forming a lower arm of the staple, and having a connecting segment between the tabs oriented substantially orthogonally to the two arms, including means facilitating movement of the lower arm of the staple, parallel to itself, and relative to the upper fixed arm, and means facilitating fastening of the lower arm in any selected position along said movement; said means facilitating movement further including a dovetail joint between a first portion of the connecting segment orthogonal to the upper arm and a second portion of the connecting segment orthogonal to the lower arm; said movement of the portion being capable of being manually carried out.

2. An adjustable staple as in claim 1 wherein the fastening means comprises socket head screw means for fastening the lower moveable arm with respect to the upper fixed arm.

3. An adjustable lower as claimed in claim 1 wherein the staple movable arm can be fitted on the portion pertaining to the fixed arm in a reversed position, that is in such a way as to present the movable arm in a decidedly nearer position to the parallel fixed arm, to allow for, as a limit, the contact between the two arms of the staple.

* * * * *

UNITED STATES PATENT AND TRADEMARK OFFICE
CERTIFICATE OF CORRECTION

PATENT NO. : 4,913,144

DATED : April 3, 1990

INVENTOR(S) : Nilli Del Medico

It is certified that error appears in the above-identified patent and that said Letters Patent is hereby corrected as shown below:

In Column 1, line 63 after the words "parallel to" insert -- itself --;

In Column 2, line 5 after the word "head" delete the word "screws" and insert therefore -- screw means --;

In Column 2, line 8 after the words "having the" insert the word -- same --;

In Column 2, line 41 after the words "forming a" insert the word -- lower --;

In Column 2, line 43 after the word "orthogonally" insert the word -- to --.

Signed and Sealed this

Twenty-eighth Day of May, 1991

*Attest:*

*Attesting Officer*

HARRY F. MANBECK, JR.

*Commissioner of Patents and Trademarks*